United States Patent [19]

Schneider

[11] 4,017,521

[45] Apr. 12, 1977

[54] PROCESS FOR THE MANUFACTURE OF MALEIC ANHYDRIDE USING HIGH SURFACE AREA CATALYST

[75] Inventor: Ronald A. Schneider, Berkeley, Calif.

[73] Assignee: Chevron Research Company, San Francisco, Calif.

[22] Filed: May 11, 1973

[21] Appl. No.: 359,294

Related U.S. Application Data

[63] Continuation-in-part of Ser. No. 263,883, June 19, 1972, abandoned.

[52] U.S. Cl. .................. 260/346.8 A; 260/346.4
[51] Int. Cl.² .................................. C07D 307/60
[58] Field of Search ................. 260/346.8 A, 346.4

[56] References Cited

UNITED STATES PATENTS

| | | | |
|---|---|---|---|
| 2,773,921 | 12/1956 | Rylander et al. | 260/346.8 |
| 3,156,707 | 11/1964 | Kerr | 260/346.8 |
| 3,293,268 | 12/1966 | Bergman et al. | 260/346.8 |
| 3,478,063 | 11/1969 | Friedrichsen et al. | 260/346.8 |
| 3,915,892 | 10/1975 | Harrison | 260/346.8 A |

FOREIGN PATENTS OR APPLICATIONS 2,160,859  6/1973  France .............................. 260/346.8

OTHER PUBLICATIONS

Cullis, Industrial and Engineering Chem., vol. 59, No. 12, Dec. 1967, pp. 19-27.

*Primary Examiner*—Henry R. Jiles
*Assistant Examiner*—Bernard Dentz
*Attorney, Agent, or Firm*—J. A. Buchanan, Jr.; John Stoner, Jr.; W. Keith Turner

[57] ABSTRACT

An improved vanadium-phosphorus mixed oxide is prepared by a unique method employing an organic medium. The substantial intrinsic surface area and the microcrystalline structure of the new oxide result in advantageous activity and selectivity effects in the catalysed vapor phase oxidation of n-butane to maleic anhydride. These oxides are also useful for the production of acid anhydrides from suitable hydrocarbon feeds.

7 Claims, No Drawings

PROCESS FOR THE MANUFACTURE OF MALEIC ANHYDRIDE USING HIGH SURFACE AREA CATALYST

CROSS-REFERENCE TO RELATED APPLICATION

This application is a continuation-in-part of U.S. application Ser. No. 263,883, filed June 19, 1972, now abandoned.

BACKGROUND OF THE INVENTION

1. Field of the Invention

This invention relates to an improved hydrocarbon oxidation catalyst especially suitable for use with saturated hydrocarbon feeds. More particularly, it relates to improved vanadium oxide-phosphorus oxide composites. Still more particularly, it relates to the production of maleic anhydride from n-butane in a vapor phase process employing the foregoing catalyst.

2. Prior Art Description

It is known in the art that n-butane can be used as a feed for the production of maleic anhydride. n-Butane is available from petroleum refinery streams and is a relatively inexpensive feed for a maleic process. Nevertheless, there is little or no use of n-butane as a process feed for the production of maleic anyhdride. Why is this? It appears that known catalysts for the partial oxidation of n-butane are unsatisfactory. A very active catalyst is required for the oxidation. Yet this very characteristic tends to be incompatible with the requirement that the oxidation be a selective partial oxidation rather than a total oxidation to carbon oxides. That is to say, presently known catalysts for the oxidation of n-butane to maleic anhydride have, in general, relatively poor selectivities.

Representative descriptions in the art which relate to the production of maleic anhydride from n-butane include U.S. Pat. No. 3,293,268.

THE INVENTION

A catalyst having excellent activity and improved selectivity in the oxidation of n-butane to maleic anhydride has now been found. It is a crystalline composite or complex of vanadium oxide and phosphorus oxide which has:

1. an intrinsic surface area of the mixed oxide per se in the range from about 7 to 50 square meters per gram;
2. a phosphorus to vanadium atomic ratio in the range 0.9–1.8 to 1, respectively;
3. a vanadium oxide component having an average valence for vanadium in the range plus 3.9 to 4.6; and
4. a phosphorus oxide component having an average valence for phosphorus of about plus 5.

By instrinsic surface area of the mixed oxide, as used in this description, is meant the surface area of the material itself, i.e., per se, and in the absence of a support or carrier.

METHOD OF PREPARATION

The novel crystalline compositions herein are pepared by precipitation of a vanado-phosphato mixed oxide complex from an essentially organic solvent medium. A minor amount of water may be present in the medium and indeed water or water-forming components bound in the precipitate are believed to be required in order to obtain a catalyst having a satisfactory selectivity and activity. The presence of a gross amount of water in the medium during the crystal-forming precipitation prevents the formation of the present novel mixed oxide catalysts having a relatively high intrinsic surface area. The precipitation is effected by evaporation of the organic solvent. The resulting crystalline solid is freed of solvent, and is then activated by heating in air for use as an oxidation catalyst. The activation procedure is required to condition the precipitated and dried mixed oxide (i.e., it is a catalyst precursor) for use as an oxidation catalyst. During the activation bound water (apparently water of hydration), or a mixture of water and organic solvent is evolved and a crystal phase change occurs.

EMDODIMENT

In a preferred method for the preparation of a crystalline vanado-phosphato mixed oxide of the invention comminuted vanadium pentoxide ($V_2O_5$) and isobutanol are charged to a glass lined reactor fitted for stirring, temperature control, the introduction of a gas into the isobutanol and for the exclusion of water vapor. For each formula weight in grams of a vanadium pentoxide, about 1 liter of the isobutanol solvent is used. The resulting slurry is then stirred and the vanadium pentoxide is dissolved in the isobutanol by passing a stream of anhydrous hydrogen chloride gas into the slurry while maintaining the temperature between 30° and 40° C. The resulting solution is red-brown colored and nearly saturated with hydrogen chloride gas. It is ready for mixing with a solution of orthophosphoric ($H_3PO_4$) acid in isobutanol.

The orthophosphoric acid solution is prepared by adding crystalline 100% orthophosphoric acid to isobutanol in a glass lined vessel large enough to accommodate the solution of vanadium oxide prepared as described above and the phosphoric acid solution. For each mol of the acid a volume of about 100 milliliters of isobutanol is desirably used. Sufficient orthophosphoric acid is charged to the vessel to yield, upon the addition of the red-brown solution of dissolved vanadium oxide, a phosphorus to vanadium atomic ratio of 1.2. The vessel should be fitted for stirring, temperature control, reflux, the introduction of the red-brown solution and for the exclusion of water vapor.

After the introduction of the red-brown solution to the phosphoric acid solution in the second vessel, the temperature of the resulting solution is increased to the reflux temperature, i.e., about 110° C., and is maintained for about 1.5 hours. Evidence of a reaction is notable in that the solution changes in color, usually to a greenish-brown. Thereafter, the reflux condenser is removed and isobutanol solvent is distilled from the reaction mixture. During the heating above at reflux and subsequently during distillation, hydrogen chloride gas evolves from the solution and is vented.

As the heating is continued and the volatiles, mainly isobutanol and hydrogen chloride, are evolved, the color of the solution continues to change; transitorally it assumes various shades of green or blue, the colorations associated with vanadium in the plus 4 valence (oxidation) state. Finally, after about two-thirds of the solvent has been evolved, the solution is colored a greenish-blue. Some light blue precipitate is usually present in the concentrate at this time. The remainder of the volatiles are conveniently removed by placing the concentrate in a loosely covered glass vessel in a ventilated oven maintained at 150° C. Drying is continued until resulting precipitated solid reaches a substantially constant weight.

The dried precipitate is a uniform, very dark green-gray solid which after activation has a surface are (BET-Method) of about 23 m²/gr. For fixed bed use it is broken up and sieved to a 20–28 mesh (Tyler Screen) size.

For the activation the following schedule is carried out:

1. Heat the precursor to 380° C. in a stream of air flowing at 1.5 volume/volume/minute. The heat input should yield a rate of temperature increase of 3° C. per minute.
2. Maintain the 380° temperature and the same air flow rate for 2 hours.
3. Increase the temperature from 380° to 480° C. at the 3° C. per minute rate of increase while passing an air-butane mixture, 1.5 volume percent of butane in air, through the bed 10 inch by 0.5 inch diameter tube) at a flow rate of 1.5 volume/volume/minute.
4. Maintain the precursor at 480° C. for about 16 hours while continuing the air-butane flow rate as before.
5. Reduce the temperature from 480° to 420° C. then increase the air-butane flow rate to a VHSV of 1000 hr.$^{-1}$ (17 vol/vol/min.).
6. Finally adjust the temperature upward or downward as required until the butane conversion is 90%.

Usually the catalyst performance stabilizes after a short run of from 6 to 36 hours. The activated catalyst has a standard activity (see discussion below) which is generally below 400° C., usually in the range 365–390° C. and a surface area (BET) of about 23 square meters per gram. This catalyst usually produces 105 kilograms of maleic anhydride per 100 kilograms of n-butane fed to the reactor or 117 kilograms of maleic anhydride per 100 kilograms of n-butane converted.

STANDARD CATALYST TEST

In order to obtain a reliable comparison of oxidation catalysts herein, a standard test was required and developed. Ten milliliters of 20/28 mesh mixed oxide was charged to a one-half inch stainless steel reactor. After activation, performance was measured at a space velocity (volume at 0° C. and 1 atm/volume/hr) of 1000 hr.$^{-1}$ using a feed of 1.5 volume percent n-butane in air. The catalyst was left onstream until its performance changed very little over a 24 hour period.

As the index of activity, I define "standard activity" as that temperature required for 90% conversion under the above conditions. Yield is defined as pounds of maleic anhydride produced per 100 pounds of hydrocarbon fed, and selectivity as pounds of maleic anhydride produced per 100 pounds of feed converted.

SURFACE AREA

Depending upon variations in the organic solvent system employed and in some degree upon the activation procedure, the surface area [BET Method — cf., H. Brunaur, P. H. Emmett, and E. Teller, JACS., Volume 60, Page 309 (1938)] ranges from 7 to 50 square meters per gram and higher. The preferred mixed oxide catalysts have surface areas in the range from 10 to 50 m²/gr and higher. In general, the higher the intrinsic surface area, the more active is the catalyst, and the lower is the temperature at which the catalyst is satisfactory for use in the oxidation of a saturated hydrocarbon feed.

P/V ATOMIC RATIO

The precipitated mixed oxides herein should have an atomic ratio, phosphorus to vanadium, which in general is in the range from 0.9–1.8 to 1, preferably 1.0–1.5 to 1, respectively.

AVERAGE VALENCE OF VANADIUM COMPONENT

The average valence of the vanadium in the activated mixed oxides of the invention is, in general, in the range from 3.9 to 4.6. Better results are believed to obtain when the average valence is in the range 4.1 to 4.4.

B-PHASE CONTENT

The selectivity of the oxidation catalysts herein was found to be directly related to the proportion of the composite which was of a particular crystal structure. For purposes of reference and since no mention or recognition of this composite structure appears to be in the art, it is designated as the B-phase. The crystals having the B-phase structure exhibit a characteristic powder x-ray diffraction pattern (CuK$\alpha$), as listed in Table I below:

TABLE I

| d (Angstrom) | Line Position 2θ, Degrees | Intensity, I |
| --- | --- | --- |
| 6.3 | 14.2 | 10 |
| 4.8 | 18.5 | 7 |
| 3.9 | 23.0 | 100 |
| 3.13 | 28.5 | 58 |
| 2.98 | 30.0 | 29 |
| 2.65 | 33.8 | 7 |

The dimensions of the unit cell for B-phase, as obtained from the complete powder x-ray diffraction data, are $a = b = 19.2$ A and $c = 7.8$ A. The crystalline phase is of hexagonal structure.

The phosphorus-vanadium mixed oxides which have a B-phase content of at least 25 percent and an intrinsic surface area in the range above 10 m²/gr. exhibit good activities and selectivities in the vapor phase partial oxidation of saturated hydrocarbon feeds. Consequently, these composites are preferred. Those having a B-phase content in excess of 50 percent exhibit, in general, excellent activites and selectivities and are most preferred. The relative amount of B-phase in a given composite is conveniently measured by the method of the National Bureau of Standards (Reference, United States Department of Commerce, N.B.S., Monograph 25, Section 6, Page 3). In the method $\alpha$-alumina is used as an internal standard, and the x-ray diffraction pattern for a 5:1 (weight) mixture of mixed oxide and $\alpha$-alumina is obtained. The ratio of the intensity (I) of the $d = 3.9$ A line of the mixed oxide to the $d = 2.085$ A line of the $\alpha$-alumina standard is a measure of the relative amount of the B-phase content for a given composite. With a sample of mixed oxides having approximately 100% B-phase, the ratio of intensities is 3.1. If the B-phase content is 25 percent, then the ratio is approximately 0.8.

The following examples further illustrate the invention.

The mixed oxide compositions herein may be prepared by a variety of reagents using a substanially organic medium. Table II below includes a number of representative reactant combinations for the preparation of vanadium-phosphorus mixed oxides. In Table IV, Examples 1–14 illustrate the use of a variety of representative organic solvents for the production of mixed oxides having a high intrinsic surface area. Examples 15–19 illustrate the effect of water upon the catalyst surface area and/or activity. Examples 20 and 21 are examples of catalysts prepared in the absence of a solvent.

TABLE II

| REACTANTS | DESIGNATOR |
|---|---|
| 1. $VOCl_3 + 1.2\ H_3PO_4 + X\ H_2O$ | A |
| 2. ½ $V_2O_5 + 1.2\ POCl_3 + X\ H_2O$ | B |
| 3. ½ $V_2O_5 + 1.2\ H_3PO_4 + X\ H_2O + HCl$ (excess)[a] | C |
| 4. $NH_4VO_3 + 1.2\ POCl_3 + XH_2O$ | D |
| 5. ½ $V_2O_5 + 0.5\ PCl_3 + 0.7\ H_3PO_4 + X\ H_2O + HCl$ (excess)[a] | E |
| 6. ¼ $V_2O_3 + ¼\ V_2O_5 + 1.2\ H_3PO_4 + X\ H_2O + HCl$ (excess)[a] | F |
| 7. $V_2O_5 + H_3PO_4$ (85%) | G |

[a]Gaseous HCl bubbled into reactants until dissolution of $V_2O_5$.

In Table III below are listed the preparative methods employed for the several combinations of reactants listed above and a designator. The two designators, a capital letter for reactants, and a numeral for method, are used to identify the mixed oxides in Table IV below.

TABLE III

| METHOD OF PREPARATION | DESIGNATOR |
|---|---|
| 1. Preparing a solution, then boiling off the solvent to leave a solid mass. | (1) |
| 2. Preparing a solution, boiling off part of the solvent, and collecting the resulting precipitate. | (2) |
| 3. Mixing the reactants without solvent. | (3) |
| 4. Mixing the reactants without solvent and fusing at 900° C. for 2 hours. | (4) |

Examples 1–13 illustrate that a mixed oxide complex of vanadium oxide and phosphorus oxide having a relatively high intrinsic surface area, for example in the range above 7 square meters per gram, and a B-phase content above 25 percent, has an excellent activity and selectivity as a catalyst for the partial oxidation of n-butane to maleic anhydride.

EXAMPLES 22–28

In the manner described in the preferred embodiment, a series of mixed oxide complexes was prepared, activated, and tested except that the phosphorus to vanadium (P/V) atomic ratios of the complexes were varied as follows: 0.9, 1.0, 1.1, 1.2, 1.3, 1.5, and 1.8. The resulting comparative data for the activated catalysts is listed below in Table V.

TABLE IV

| EX. NO. | REACTANTS AND METHOD | MOLS WATER ADDED "X" | SOLVENT[1] | STANDARD CATALYST PERFORMANCE[9] | | | ACTIVATED CATALYST | | |
|---|---|---|---|---|---|---|---|---|---|
| | | | | CONV. % | TEMP. °C. | YIELD[2] WT. % | SURFACE AREA (BET, m²/g) | OXIDATION STATE OF VANADIUM | B-PHASE[10] % |
| 1 | A-1 | 1.2 | THF[3] | 90 | 430 | 104 | 19 | 4.1 | 88 |
| 2 | B-1 | 3.6 | THF[3] | 90 | 408 | 98 | 18 | 4.2 | 83 |
| 3 | A-1 | 0 | THF[3] | 90 | 420 | 96 | 22 | 4.1 | 90 |
| 4 | C-1 | 0 | Isobutanol | 90 | 374 | 105 | 23 | 4.2 | 73 |
| 5 | B-1 | 3.6 | 1,2-Dimethoxy-ethane | 90 | 452 | 97 | 12 | 4.4 | 42 |
| 6 | B-1 | 3.6 | 1,2-Dimethoxy-ethane[4] | 90 | 422 | 89 | 15 | — | — |
| 7 | B-1 | 3.6 | 1,2-Dimethoxy-ethane[5] | 90 | 404 | 93 | 21 | 4.1 | — |
| 8 | C-1 | 0 | Methanol | 90 | 468 | 90 | 8 | 4.3 | 81 |
| 9 | C-1 | 0 | Acetic Acid[6] | 90 | 465 | 76 | 10 | — | — |
| 10 | D-1 | 3.6 | 1,2-Dimethoxy-ethane | 90 | 472 | 73 | 11 | — | 27 |
| 11 | C-1 | 0 | Acetic Acid[8] | 90 | 446 | 73 | 15 | — | — |
| 12 | F-1 | 0 | $ClCH_2CH_2Cl$:Methanol::2:1 | 90 | 446 | 76 | 10 | — | — |
| 13 | B-1 | 3.6 | Acetone | 90 | 553 | 25 | 15 | 4.6 | — |
| 14 | F-1 | 0 | Ethyl Acetate:Ethanol:Acetic Acid 10:6:1 | 85 | 510 | 54 | — | 4.1 | — |
| EFFECT OF WATER | | | | | | | | | |
| 15 | F-1 | 0 | Acetic Anhydride | 16 | 510 | — | 5 | 4.6 | — |
| 16 | E-1 | 0 | Acetic Acid + $Ac_2O$[7] | 38 | 510 | 23 | 16 | 3.9 | — |
| 17 | E-2 | 2.0 | Acetic Acid | 90 | 399 | 92 | 15 | 4.2 | — |
| 18 | C-1 | 5.0 | Acetic Acid:$H_2O$ = 16:3[8] | 90 | 424 | 83 | 11 | — | — |
| 19 | F-1 | 20 | Propionic Acid:$H_2O$ = 2:3 | 49 | 510 | 42 | 5 | — | — |
| 20 | G-3 | — | None | 90 | 532 | 40 | 3 | 4.1 | 40 |
| 21 | G-4 | — | None | 48 | 536 | 17 | — | 4.5 | — |

NOTES
[1]500 mls of solvent used per gram atom of phosphorus. Solvent ratios are by volume.
[2]Based on butane fed.
[3]Tetrahydrofuran.
[4]33 Wt. % maleic acid, based on $V_2O_5$, added.
[5]66 Wt. % bis-(2-methoxyethyl)ether, based on $V_2O_5$, added.
[6]2 mols paraformaldehyde per mol $V_2O_5$.
[7]4 mols acetic anhydride per mol $V_2O_5$.
[8]1 mol of benzaldehyde added per mol of $V_2O_5$.
[9]Catalyst performance determined at a space velocity of 1,000 hrs.⁻¹ (STP) and using 1.5 volume percent of n-butane in air.
[10]As measured by x-ray diffraction.

TABLE V

| EX. NO. | ATOMIC RATIO, P/V | STD. ACTIVITY ° C. | SURFACE AREA, m²/gr. | B-PHASE[1] % | YIELD,[2] WT.% |
|---|---|---|---|---|---|
| 22 | 0.9 | 540 | — | 0 | 15 |
| 23 | 1.0 | 419 | — | 48 | 83 |
| 24 | 1.1 | 392 | 27 | 76 | 94 |
| 25 | 1.2 | 373 | 16 | 53 | 99 |
| 26 | 1.3 | 403 | 20 | 42 | 87 |
| 27 | 1.5 | 475 | 12 | 28 | 65 |
| 28 | 1.8 | 511 | — | 0 | 39 |

[1] By x-ray diffraction analysis.
[2] Based on butane fed at the standard activity temperature.

These examples demonstrate that both the yield and the activity of the catalyst composites are directly related to the B-phase content.

EXAMPLES 29–35

Using a catalyst prepared in the manner described in the embodiment, and a space velocity of 1000 hr$^{-1}$, and a feed of 1.5 volume percent hydrocarbon in air, other hydrocarbon feeds were oxidized. The feeds and resullts obtained are listed in Table VI below.

TABLE VI

| EX. NO. | FEED COMPOUND | TEMP. ° C. | CONV. % | YIELD WT. % |
|---|---|---|---|---|
| 29 | n-pentane | 368 | 90 | 64 |
| 30 | isopentane | 380 | 80 | 56 |
| 31 | methylcyclo-pentane | 380 | 91 | 63 |
| 32 | 2-butene | 375 | 99 | 85 |
| 33 | butadiene | 335 | 100 | 86 |
| 34 | benzene | 417 | 92 | 55 |
| 35 | o-xylene | 358 | 90 | (1) |

(1) 31% phthalic plus 8% maleic anhydride.

The examples in Table VI and the above-described examples in which an n-butane feed was oxidized to maleic anhydride demonstrate that the novel catalyst compositions herein are useful as catalysts for the partial oxidation of a suitable hydrocarbon feed with molecular oxygen for the production of maleic or phthalic anhydride. Suitable hydrocarbon feeds include aromatic hydrocarbons containing up to 10 carbon atoms as exemplified by o-xylene and naphthalene and saturated or mono- or diolefinic acyclic or cyclic hydrocarbons which have a carbon atom content in the range 4 to 10 and a linear chain of at least 4 carbon atoms.

The high surface phosphato-vanado mixed oxide complexes herein exhibit, in general, long catalyst lives and excellent retention of selectivity. After the initial breaking in of the activated catalyst, long periods of continuous use are indicated. Thus, over a period of 1200 hours on stream, a representative catalyst has been used without evidence of appreciable deactivation or loss of activity. Estimated useful lives for these catalyst exceed 8 months and probably are 16 months or more.

The fixed bed or fluid bed process conditions normally employed for the partial oxidation of a hydrocarbon feed are, in general, satisfactory for use with the high surface mixed oxides of the invention as follows:

| CONDITION | RANGE |
|---|---|
| Temperature, ° C. | 300–500, preferably 325–490 |
| Pressure, atm. | 0.5–10, preferably 1–5 |
| Contact time, sec. | 0.05–5, preferably 0.1–2; | and a feed mixture, air plus hydrocarbon, or oxygen-containing gas plus hydrocarbon which is outside the explosive range.

In view of the exceptional activities of the high surface mixed oxides of the invention, they are especially effective for use as catalyst for the partial oxidation of n-butane. The oxidation conditions in this case desirably include a temperature in the range 350–490° C., preferably 375–475° C., and the other condition, as noted above. n-Butane-air feed mixtures which contain an amount of n-butane in the range 0.5 to 1.8 volumes per 100 volume of air are preferred feed mixtures for use in fixed bed reactors. In the case of fluid bed reactors, a more concentrated feed stream is satisfactory and the range of the hydrocarbon to air volume ratio may be as much as 0.5–10 to 100.

The mixed oxides of the invention may be sized as desired in the usual manner, grinding, screening and the like, and employed. They may also be comminuted, slurried in a suitable liquid medium, and extruded or pelleted as desired. Similarly, they may be comminuted, slurried in a suitable liquid medium with or without an ordinary binding agent and shaped as desired, for example in spheres, or disposed upon a suitable inert support such as alumina, titania, silicon carbide, silica kieselguhr, pumice and the like. Alternatively, the mixed oxide may be disposed upon an inert carrier by adding the carrier to a concentrate of the oxides in an essentially organic medium and evaporating the organic solvent.

Clearly, modifications and variations of the invention as hereinbefore set forth and exemplified may be made without departing from the sense thereof. Therefore, only such limitations should be imposed as are indicated in he appended claims.

I claim:

1. A process for producing maleic anhydride, which comprises partially oxidizing a hydrocarbon feed selected from the group consisting of aromatic and saturated or mono- or diolefinic acyclic or cyclic hydrocarbons having a carbon atom content in the range 4 to 10 and a linear chain of at least 4 carbon atoms, at a temperature in the range from about 300° to 500° C. by contacting a mixture of said feed and air or of said feed and a molecular oxygen-containing gas with a crystalline phosphorus-vanadium mixed oxide catalyst composition containing phosphorus, vanadium and oxygen, wherein the catalyst is effective for catalyzing the oxidation of the feed to maleic anhydride and wherein the catalyst is characterized by vanadium having an average valence in the range from about plus 3.9 to 4.6, a phosphorus to vanadium atomic ratio in the range from about 0.9–1.8 to 1, and an intrinsic surface area in the range from about 10 to 50 square meters per gram.

2. A process as in claim 1 wherein said feed is n-butane and said temperature is in the range from about 350° to 490° C.

3. A process as in claim 1 wherein said feed is n-butane and said temperature is in the range from about 375° to 475° C.

4. A process as in claim 1 wherein said mixed oxide has a B-phase content in excess of about 25 percent and wherein the B-phase exhibits a characteristic powder x-ray diffraction pattern having $d$-spacing peaks comprising 6.3, 4.8, 3.9, 3.13, 2.98 and 2.65 A.

5. A process as in claim 1 wherein said feed is benzene.

6. A process as in claim 3 wherein said mixed oxide has a B-phase content in excess of about 25 percent wherein the B-phase exhibits a characteristic powder x-ray diffraction pattern having $d$-spacing peaks comprising 6.3, 4.8, 3.9, 3.13, 2.98 and 2.65 A.

7. A process in accordance with claim 4 wherein said feed is n-butane.

* * * * *